(12) United States Patent
Rafferty et al.

(10) Patent No.: US 6,893,455 B1
(45) Date of Patent: May 17, 2005

(54) COOLING BAND

(76) Inventors: Sharon R. Rafferty, 36 Sherman Dr., Malvern, PA (US) 19355; Sheila R. Piernock, 14 Sycamore Ct., Paoli, PA (US) 19301

( * ) Notice: Subject to any disclaimer, the term of this patent is extended or adjusted under 35 U.S.C. 154(b) by 0 days.

(21) Appl. No.: 10/732,054

(22) Filed: Dec. 10, 2003

(51) Int. Cl.[7] .................................................. A61F 7/00
(52) U.S. Cl. ........................................ 607/114; 607/108
(58) Field of Search ........................ 607/108–112, 114

(56) References Cited

U.S. PATENT DOCUMENTS

| | | | |
|---|---|---|---|
| 2,925,719 A | 2/1960 | Robbins et al. | 62/4 |
| 3,643,665 A | 2/1972 | Cailoutte | 128/403 |
| 4,204,543 A | 5/1980 | Henderson | 128/402 |
| 4,382,446 A | 5/1983 | Truelock et al. | 128/402 |
| 4,484,363 A | 11/1984 | Varanese | 2/209.1 |
| 4,566,455 A | 1/1986 | Kramer | 128/380 |
| 4,742,581 A | 5/1988 | Rosenthal | 2/181 |
| 4,765,338 A | 8/1988 | Turner et al. | 128/402 |
| 4,815,144 A | 3/1989 | Martin | 2/7 |
| 5,305,470 A | 4/1994 | McKay | 2/7 |
| 5,327,585 A | 7/1994 | Karlan | 2/7 |
| 5,456,703 A | 10/1995 | Beeuwkes, III | 607/109 |
| 5,572,745 A | 11/1996 | Mainus | 2/171.2 |
| 5,956,759 A | 9/1999 | Benedict | 2/7 |
| 6,598,236 B1 | 7/2003 | Gantt | 2/171.3 |

*Primary Examiner*—Roy D. Gibson
*Assistant Examiner*—Aaron Roane
(74) *Attorney, Agent, or Firm*—Michael F. Petock, Esq.

(57) ABSTRACT

An apparatus for cooling a portion of the anatomy of a wearer comprises an elongated fabric with fastening means on its ends for adjustably connecting the ends together in the form of a closed loop to encircle tightly a portion of the anatomy of the wearer such as the head or wrist. A portion of elongated fabric is provided with a pocket with a flap for folding over an elongated cooling pack. A cooling pack is inserted in the pocket and retained in the pocket by the flap. The cooling pack is comprised of a plurality of elongated tubes, at least some of the tubes containing ammonium nitrate and a container for water. A burstable seal is provided between the container for the water and the tubes containing the ammonium nitrate. Pressure may be applied to burst the seals allowing the water to mix with the ammonium nitrate and cause an endothermic cooling reaction.

15 Claims, 3 Drawing Sheets

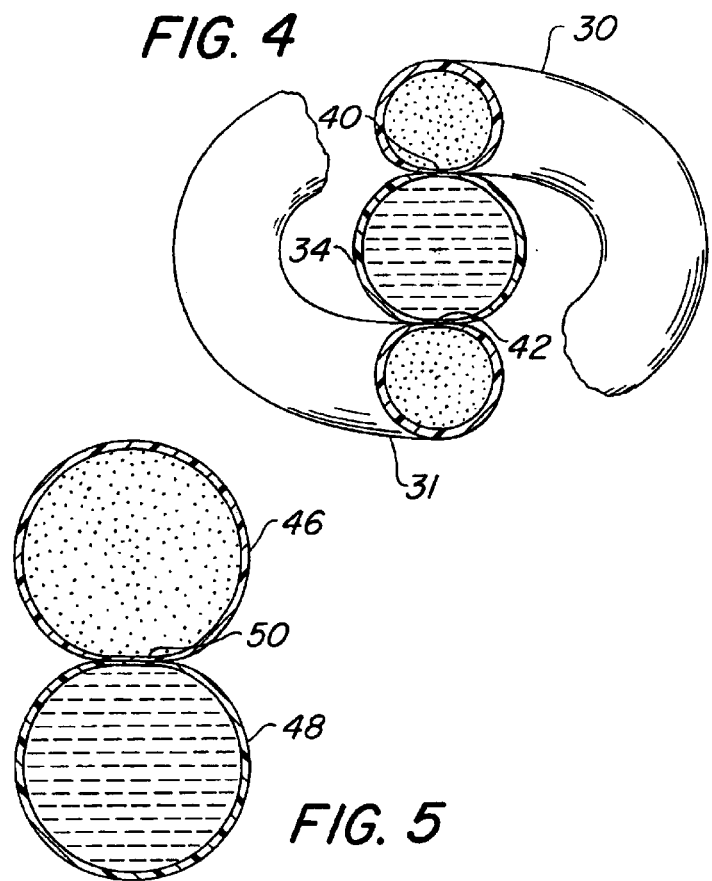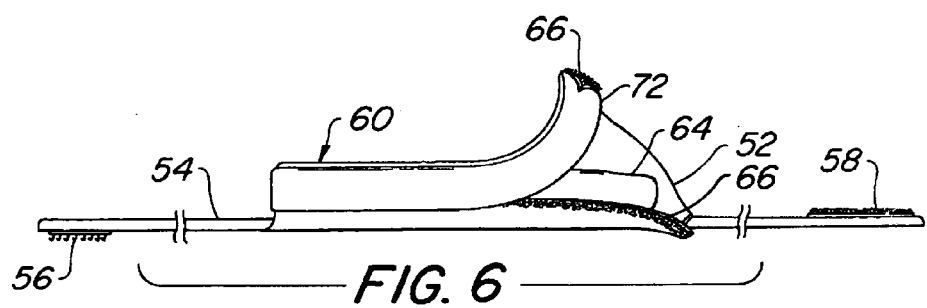

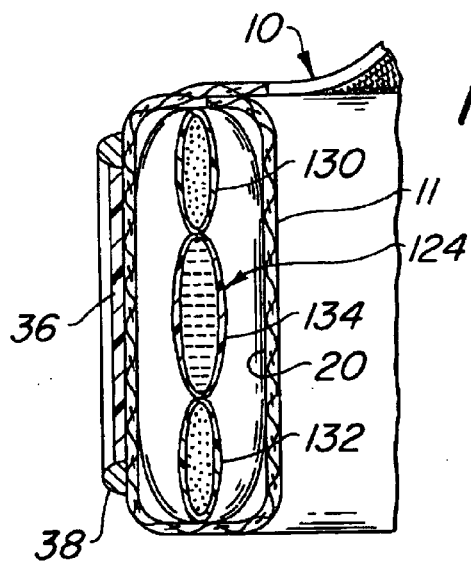
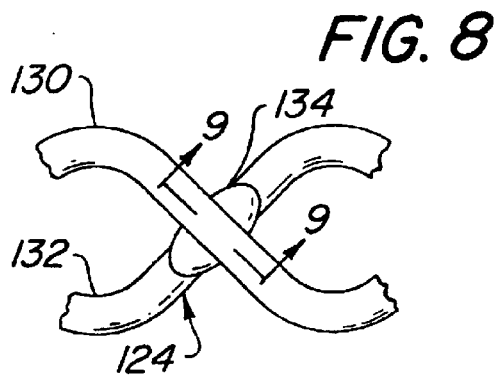
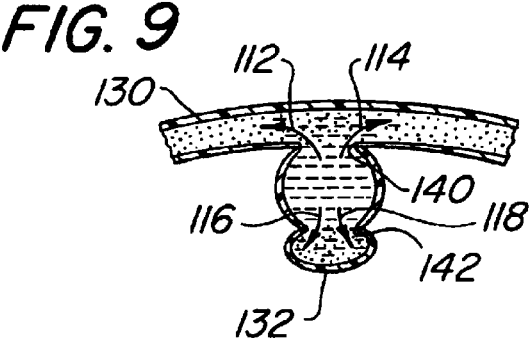
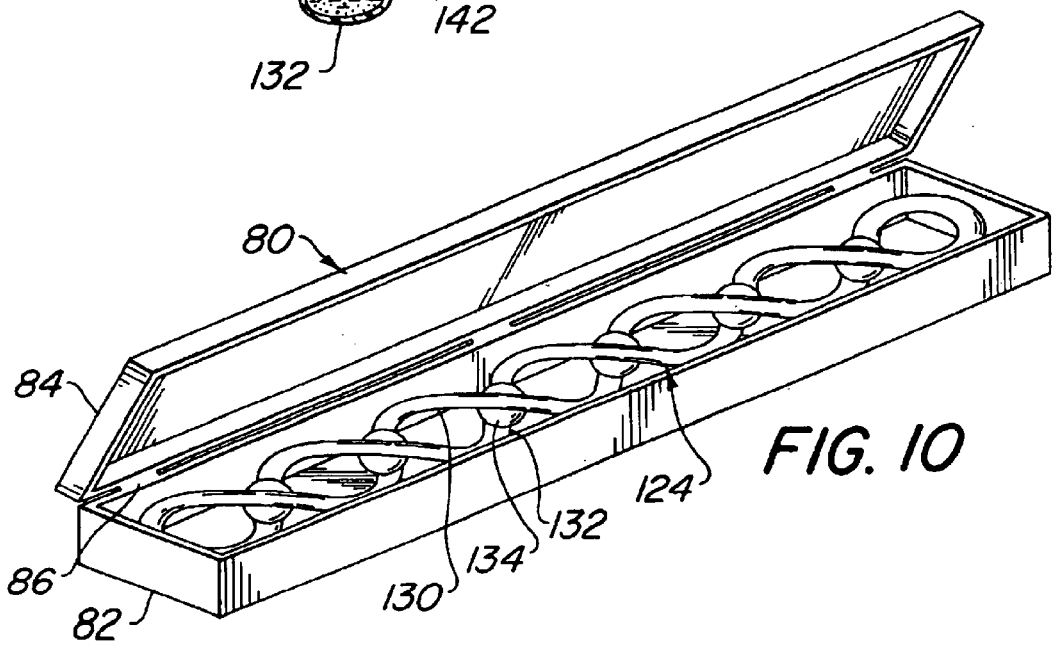

COOLING BAND

FIELD OF THE INVENTION

The present invention relates to a cooling band. More particularly, the present invention relates to a cooling band which may be utilized to encircle and cool a portion of the anatomy over an extended period of time.

BACKGROUND OF THE INVENTION

When people exert themselves or exercise such as by playing soccer, running, jogging, playing tennis or other exerting activities, they generate significant body heat. A disproportionately large portion of the heat flows to the head of a person from which it is normally dissipated. However, particularly during warm weather and with strenuous exertion, the heat is not sufficiently dissipated to prevent overheating.

Further, any means to try to help dissipate the heat must be a means which may be worn during the activities. Further, such means or apparatus is desired to have a pleasing or attractive appearance. Further, any such device should not be too cold such that it may cause frostbite or undue cooling, should not be too heavy and should maintain a cooling effect for an extended period of time.

SUMMARY OF THE INVENTION

An advantage of the present invention is that it may be utilized to provide a cooling effect to various parts of the anatomy of a wearer including areas such as the head, wrist or ankles.

Another advantage of the present invention is that it provides a regulated cooling effect which will not be too cold.

Another advantage of the present invention is that it provides a means of providing a cooling effect over an extended period of time.

Another advantage of the present invention is that it provides an attractive wearable band.

Another advantage of the present invention is that a cooling band is provided which is not too heavy.

Briefly and basically, in accordance with the present invention, an apparatus is provided for cooling a portion of the anatomy of a wearer which comprises an elongated fabric having a first and a second end. A first fastening means is mounted on the first end and the second end where the first end and the second end may be adjustably connected together to adjust the length of a closed loop formed by the elongated fabric to encircle tightly a portion of the anatomy of the wearer such as the head or wrist. A portion of the elongated fabric is provided with a pocket with a flap for folding over an elongated cooling pack. The flap is provided with a second fastening means for securing the flap. The cooling pack is inserted in the pocket and retained in the pocket by the flap. The cooling pack is comprised of a plurality of elongated tubes, at least one of the tubes containing ammonium nitrate. A container for water is provided. A burstable seal is provided between the container and the tubes containing the ammonium nitrate. Pressure may be applied to the tubes and/or the container for water to burst the seals allowing the water to mix with the ammonium nitrate and cause an endothermic cooling reaction.

In accordance with one embodiment of the present invention, since a plurality of small tubes are utilized, the cooling rate may be controlled and the cooling may be extended over a period of time. Additional pressure may be applied from time to time to burst more seals allowing the cooling to be regulated to proceed at a controlled rate wherein the band does not become too cold and the cooling effect may be extended over an extended period of time.

The container for the water may be a bubble shaped container formed between two tubes containing ammonium nitrate with burstable seals being provided between the bubble shaped container and the tubes. Alternatively, some of the tubes may contain ammonium nitrate and other tubes may contain water with ammonium nitrate and water tubes being joined with a burstable seal therebetween.

In accordance with a presently preferred embodiment, a hook and loop fastener may be utilized to seal the flap of the pocket and also at the ends of the band to provide the adjustable closed loop.

In accordance with a presently preferred embodiment, the pocket on the headband may extend for substantially the full length of the elongated fabric. The cooling pack would be of a length substantially equivalent to the length of the pocket. In this manner, the cooling pack may extend substantially all of the way around the head of the wearer or around the wrist of the wearer.

Alternatively, the pocket may extend for a distance substantially less than the length of the elongated fabric with the cooling pack being of a length substantially equivalent to the length of the pocket whereby the cooling pack extends substantially from temple to temple of a wearer in the case of a headband.

In a presently preferred embodiment, the outer surface of the pocket is provided with a metallic plastic decorative panel which creates a pleasing appearance. The circumference of the metallic plastic decorative panel may be encircled with cording to provide an additional pleasing effect.

In a presently preferred embodiment, the fabric of the headband or wrist band is made of terry cloth.

In one embodiment of the present invention, the plurality of tubes and the container for water, whether the container be tubing or a capsule, may be enclosed within an impervious envelope. A plurality of tubes and water containers may be contained within the impervious envelope.

In a presently preferred embodiment, a substantially rigid container would be provided for the cooling pack for storage prior to insertion into the pocket of the headband. In this manner, any possible accidental bursting of the seals between the container for the water and the tube or tubes containing ammonium nitrate would be avoided.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

FIG. 4 is a cross sectional view taken along line 4—4 of FIG. 3.

FIG. 5 is a cross sectional view of another embodiment of cooling tubes corresponding to the view of FIG. 4.

FIG. 6 is a plan view, partially broken away, and illustrating a cooling pack being inserted into a pocket of that embodiment.

FIG. 7 is a cross sectional view of a preferred embodiment of the invention taken a long line 2—2 of FIG. 1.

FIG. 8 is a plan view of a portion of intertwined tubes containing ammonium nitrate with a container for water formed therebetween.

FIG. 9 is a cross sectional view taken along line 9—9 of FIG. 8 illustrating the flow of water in four directions into the two intertwined tubes containing ammonium nitrate upon bursting of the burstable seals between a container for water and tubes containing ammonium nitrate.

FIG. 10 is a view in perspective of a substantially rigid container for storing a cooling pack prior to insertion of the cooling pack into the cooling band pocket.

DETAILED DESCRIPTION OF THE PREFERRED EMBODIMENTS

Figure 1:
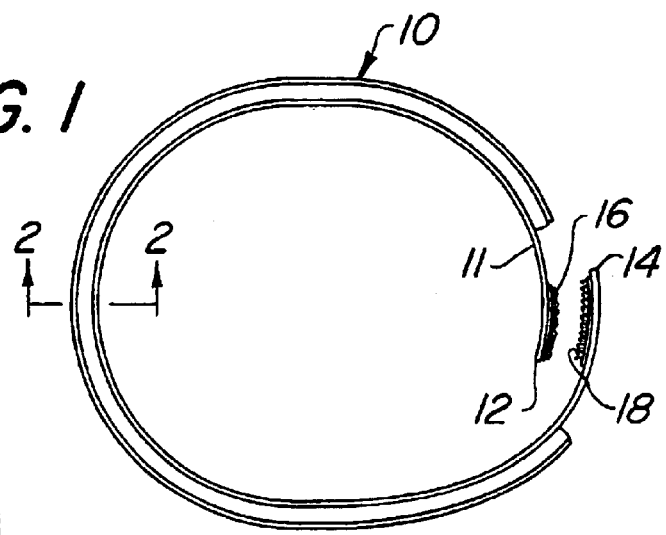
FIG. 1 is a plan view of a cooling band in accordance with the present invention.

Referring now to the drawings wherein like numerals indicate like elements, there is shown in FIG. 1 an apparatus or cooling band 10 for cooling a portion of the anatomy of a wearer. Apparatus 10 may be a headband, wristband, an ankle band or any other band for tightly encircling a portion of the anatomy of a wearer. Apparatus 10 is comprised of an elongated fabric 11 having a first end 12 and a second end 14. First end 12 and second end 14 are provided with fastening means 16 and 18, respectively, where first end 12 and second end 14 may be adjustably connected together to adjust the length of a closed loop formed by the elongated fabric to encircle tightly a portion of the anatomy of the wearer. In a presently preferred embodiment, the first fastening means comprised of fastening means 16 and 18 may preferably be comprised of a hook and loop fastener, such as 18 being comprised of hooks and 16 being comprised of loops, such as that which is commercially available under the trademark "VELCRO". However, it is understood that various other types of fasteners may be utilized including a plurality of snaps which may be selectively snapped to adjust the size of the closed loop, buckles, clamps, buttons or any other suitable fastener. It is desired that apparatus or band 10 tightly encircle a portion of the anatomy of the wearer to retain the apparatus firmly in place even when the wearer is engaged in activities such as playing soccer, tennis or the like. However, it is understood that apparatus or band 10 may be provided with a limited degree of elasticity, but in a presently preferred embodiment, elasticity would not be provided in the fabric in order to maximize the ability of the band to tightly encircle a body part and prevent movement of the band on the wearer, particularly where the band may be utilized as a headband.

Figure 2:
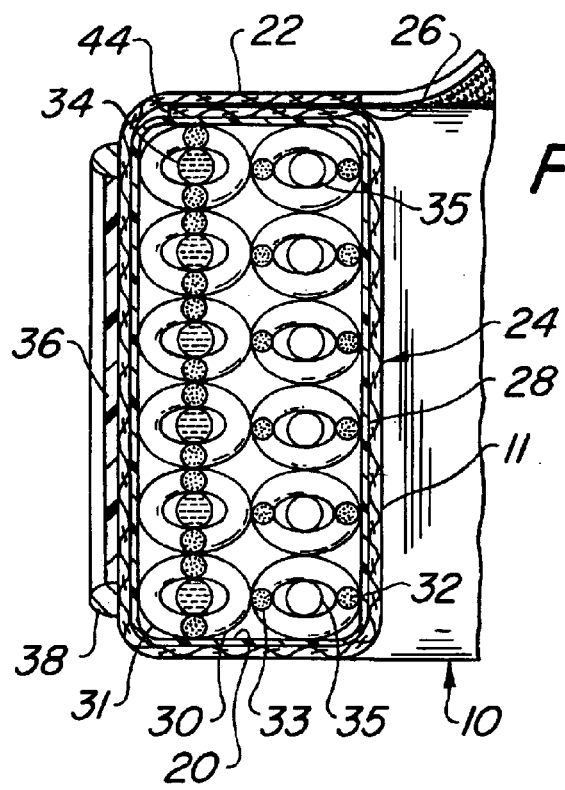
FIG. 2 is a cross sectional view taken along line 2—2 of FIG. 1.

A portion of the elongated fabric which makes up the band 10 is provided with a pocket 20 best illustrated in FIG. 2. Pocket 20 is provided with a flap 22 for folding over an elongated cooling pack 24. Flap 22 is provided with a second fastening means 26 for securing the flap to the elongated fabric 11. Second fastening means 26 may also be a hook and loop fastener or any other suitable fastener for retaining flap 22 in a closed position. As illustrated in FIG. 2, flap 22 may seal to an extension 44 of elongated fabric 11. The cooling pack 24 is inserted into pocket 20 and is retained in pocket 20 by flap 22.

As illustrated in FIG. 2, the cooling pack in one embodiment may be comprised of an impervious envelope 28 containing a plurality of elongated tubes 30, 31, 32 and 33. At least some of the tubes contain ammonium nitrate. Containers 34 and 35 for water are contained within the impervious envelope 28. Burstable seals 40 and 42, as best seen in FIG. 4, are provided between the container 34 and the tubes 30 and 31 containing ammonium nitrate. Pressure may be applied to impervious envelope 28 to burst burstable seals 40 and 42 allowing the water to mix with the ammonium nitrate and cause an endothermic cooling reaction.

The front outer surface of apparatus or band 10 may preferably be provided with a metallic plastic decorative panel 36. Metallic plastic is commercially available and provides a pleasing appearance. This provides an appearance similar to metallic paint and may be brightly colored. Various colors may be selected for use on the metallic plastic decorative panel 36. Further, to enhance the aesthetic appearance of cooling band apparatus 10, metallic plastic decorative panel 36 may be provided with cording 38 on its periphery or circumference.

Figure 3:
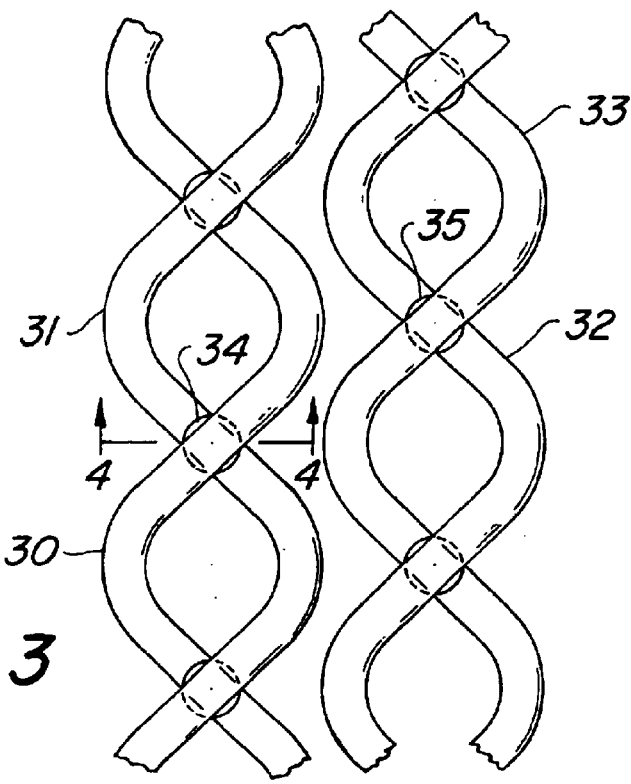
FIG. 3 is a plan view of one embodiment of intertwined or interwoven cooling tubes in accordance with the present invention.

Referring now more particularly to FIGS. 2, 3 and 4, with respect to the structure of the cooling pack, FIG. 3 illustrates one example of tubing for containing ammonium nitrate being intertwined or interwoven with containers for water being juxtaposed between the intertwined tubing. More specifically, there is shown in FIG. 3 intertwined tubing 30 and 31 with water container 34 formed therebetween. The structure of the intertwined tubing with the water container 34 therebetween is best illustrated in FIG. 4. As described above, burstable seals 40 and 42 are provided between container 34 for the water and tubing 30 and 31 for the ammonium nitrate. FIG. 2 illustrates a cross sectional view through cooling pack 24 which would correspond to the position of section line 4—4 shown in FIG. 3. Accordingly, the left column of intertwined tubes and water containers is a cross sectional view through the center of the water container 34 while the right column of tubes in FIG. 2, taken at the same position, would illustrate the cross section of ammonium nitrate tubes 32 and 33 and water container 35 in elevation. However, it is understood that various other arrangements of the tubing may be utilized. The tubing need not be intertwined, but maybe formed parallel with a water container in between. Alternatively, another arrangement is shown in FIG. 5.

Referring now to FIG. 5, there is shown a cross sectional view of another embodiment of the tubing wherein tube 46 contains ammonium nitrate and adjacent tube 48 contains water. Tubes 46 and 48 are provided with a burstable seal 50 therebetween. In the embodiment of FIG. 5, the water container is tube 48. The tubing of FIG. 5 may be intertwined in a manner similar to that illustrated with respect to FIGS. 2, 3 and 4. Alternatively, the tubing of FIG. 5 may be parallel. The cross sectional view of FIG. 5 may be taken at a point where intertwining tubes meet or may be taken at any point along the length of the tubes if the two tubes are joined in a parallel fashion.

Referring now to FIG. 6, there is shown another embodiment of an apparatus in accordance with the present invention wherein apparatus or band 60 is provided with a pocket 52 which is substantially shorter than the length of elongated fabric 54. Elongated fabric 54 is provided with the first fastening means 56 and 58 to provide an adjustable length closed loop as described with respect to the embodiment of FIG. 1. However, with the shorter pocket 52 and shorter cooling pack 64, a lighter embodiment is provided which would have a cooling pack length substantially equal to the distance from temple to temple across the forehead of a wearer. Pocket 52 of apparatus or headband 60 would be provided with a flap 72 having a second fastening means 66 similar to that described with respect to the embodiment FIG. 1.

Referring now to FIG. 7, there is shown a cross sectional view of the cooling band of FIG. 1 corresponding to section line 2—2 wherein a presently preferred embodiment of elongated cooling pack 124 is illustrated. This cooling pack 124 may be inserted into a cooling band of any of the embodiments disclosed herein including the cooling band of FIG. 1 having an elongated cooling pack with a length substantially equivalent to the length of band 10 or having a shorter cooling pack similar to cooling pack 64 of FIG. 6 which would cover the forehead from temple to temple in the case of a headband. As described above, the cooling band of the present invention may also be utilized for cooling of the wrist, ankles or other body part. In FIG. 7, cooling pack 124 is illustrated in the apparatus or cooling band 10 of FIG. 1.

As illustrated in FIG. 7, cooling pack 124 is contained within pocket 20 of cooling band 10. Cooling pack 124 is not provided with an impervious envelope. Cooling pack 124 is comprised of elongated tubes 130 and 132 containing ammonium nitrate. Tubes 130 and 132 may preferably be intertwined as illustrated in FIG. 8. Mounted between and in juxtaposition to tubes 130 and 132 is a container for water 134. The walls of tubes 130 and 132 and container 134 are preferably comprised of an impervious material. Accordingly, there is no need for an additional envelope of impervious material, although the same may be provided in the embodiment as illustrated in FIG. 2.

As described above, a burstable seal is provided between water container 134 and ammonium nitrate containing tubes 130 and 132. A plan view of the intertwined arrangement of ammonium nitrate container tubes 130 and 132 and water container or capsule 134 is illustrated in FIG. 8.

Referring now to FIG. 9, there is shown a cross sectional view taken along line 9—9 of FIG. 8 illustrating the burstable seal comprised of seals 140 and 142 in their bursted condition allowing water to flow in four directions into tubes 130 and 132 containing ammonium nitrate. For example, upon bursting of burstable seal 140, water flows from water container 134 into ammonium nitrate containing tube 130 in the directions as shown by arrows 112 and 114. Upon the bursting of seal 142, water flows in the direction of arrows 116 and 118 in two directions into ammonium nitrate containing tube 132.

Referring now to FIG. 10, there is shown a substantially rigid container 80 which may be used to house the cooling pack of any of the embodiments prior to insertion into the pocket of the cooling band, thereby preventing accidental bursting of the burstable seals and the activation of the cooling reaction by allowing water into the ammonium nitrate. Such unintentional bursting of the burstable seals at a time significantly prior to its intended use may cause the cooling reaction to dissipate prior to its intended time of use, and therefore accordingly, it is desirable to avoid such unintentional bursting of the burstable seal. Although a rigid container such as container 80 is not essential, it is preferable.

As illustrated in FIG. 10, substantially rigid container 80 may be comprised of a container 82 with a closeable lid 84. The lid 84 may be hingeably mounted to the box portion 82 as illustrated at 86 in FIG. 10. However, it is understood that various other means of providing an easily openable substantially rigid container may be utilized including one having a top which snaps on and off the lower portion. As illustrated in FIG. 10, a cooling pack 124 is contained within the box portion 82 of substantially rigid container 80. As described above with respect to FIG. 7, cooling pack 124 is comprised of ammonium nitrate containing tubes 130 and 132 and a container 134 for water. As illustrated in FIGS. 3 and 10, it is understood that a plurality of water containers may preferably be utilized.

The present invention may be embodied in other specific forms without departing from the spirit or essential attributes thereof and, accordingly, reference should be made to the appended claims, rather than to the foregoing specification as indicating the scope of the invention.

We claim:

1. An apparatus for cooling a portion of the anatomy of a wearer comprising: an elongated fabric having a first end and a second end; a first fastening means mounted on said first end and said second end where said first end and said second end may be adjustably connected together to adjust the length of a closed loop formed by said elongated fabric to encircle tightly a portion of the anatomy of the wearer; a portion of said elongated fabric being provided with a pocket with a flap for folding over an elongated cooling pack, said flap being provided with a second fastening means for securing said flap, said cooling pack being inserted in said pocket and retained in said pocket by said flap; said cooling pack being comprised of a plurality of elongated tubes, at least one of said plurality of elongated tubes containing ammonium nitrate; a container for water in juxtaposition with at least one of said plurality of tubes containing ammonium nitrate; wherein said container for water is a bubble shaped container formed between two tubes with a burstable seal being provided between said bubble shaped container and said tubes; wherein said burstable seal between said container and said tubes containing ammonium nitrate; whereby pressure may be applied to said tubes and/or container for water to burst said seal allowing said water to mix with said ammonium nitrate causing an endothermic cooling reaction.

2. An apparatus in accordance with claim 1 wherein said container for water is some of the remaining tubes, said water containing tubes and said ammonium nitrate containing tubes being joined with said burstable seal therebetween.

3. An apparatus in accordance with claim 1 wherein said first fastening means is a hook and loop fastener.

4. An apparatus in accordance with claim 1 wherein said second fastening means is a hook and loop fastener.

5. An apparatus in accordance with claim 1 wherein said apparatus is a headband and said pocket extends for substantially the full length of said elongated fabric with said cooling pack being of a length substantially equivalent to the length of said pocket whereby said cooling pack extends substantially all of the way around the head of the wearer.

6. An apparatus in accordance with claim 1 wherein said apparatus is a headband and said pocket extends for a distance substantially less than the length of the elongated fabric with said cooling pack being of a length substantially equivalent to the length of said pocket whereby said cooling pack extends substantially from temple to temple of a wearer.

7. An apparatus in accordance with claim 1 wherein said pocket is provided on its outer surface with a metallic plastic decorative panel.

8. An apparatus in accordance with claim 7 wherein said metallic plastic decorative panel is encircled by cording.

9. An apparatus in accordance with claim 1 wherein said elongated fabric is comprised of terry cloth.

10. An apparatus in accordance with claim 1 wherein said elongated fabric is provided with elasticity.

11. An apparatus in accordance with claim 1 wherein said cooling pack includes an impervious envelope containing said plurality of elongated tubes.

12. An apparatus in accordance with claim 11 wherein said impervious envelope contains a plurality of pairs of intertwined elongated tubes.

13. An apparatus in accordance with claim 1 wherein said plurality of elongated tubes are intertwined.

14. An apparatus in accordance with claim 1 wherein said cooling pack is provided with a substantially rigid container for storage of said cooling pack prior to insertion into said pocket.

15. An apparatus in accordance with claim 1 wherein said two tubes are intertwined with said bubble shaped container therebetween, upon bursting of said burstable seal, water being caused to flow in four directions into said two tubes.

\* \* \* \* \*